US008439679B2

(12) United States Patent
Hoke, III et al.

(10) Patent No.: US 8,439,679 B2
(45) Date of Patent: May 14, 2013

(54) EXTRACTOR FOR BROKEN TOOTH ROOT

(76) Inventors: Theodore John Hoke, III, Bellbrook, OH (US); Niles A. Syska, Apopka, FL (US)

( * ) Notice: Subject to any disclaimer, the term of this patent is extended or adjusted under 35 U.S.C. 154(b) by 0 days.

(21) Appl. No.: 11/906,049

(22) Filed: Sep. 28, 2007

(65) Prior Publication Data
US 2008/0090206 A1    Apr. 17, 2008

Related U.S. Application Data

(60) Provisional application No. 60/850,990, filed on Oct. 11, 2006.

(51) Int. Cl.
*A61C 3/00*    (2006.01)
(52) U.S. Cl.
USPC .......................................... 433/152; 433/153
(58) Field of Classification Search .......... 433/141–164, 433/172–176, 218–223; 81/53.2; 408/199–233; 470/1–7; 411/378, 427
See application file for complete search history.

(56) References Cited

U.S. PATENT DOCUMENTS

| | | | | |
|---|---|---|---|---|
| 2,210,349 A | * | 8/1940 | Beeck | 433/152 |
| 2,488,036 A | * | 11/1949 | Pofcher | 433/152 |
| 5,651,675 A | * | 7/1997 | Singer | 433/172 |
| 6,019,602 A | * | 2/2000 | Fletcher et al. | 433/152 |
| 6,666,684 B1 | * | 12/2003 | Names | 433/173 |
| 2002/0039717 A1 | * | 4/2002 | Amber et al. | 433/172 |
| 2004/0157190 A1 | * | 8/2004 | Fiumana | 433/159 |
| 2005/0178245 A1 | * | 8/2005 | Kozak | 81/53.2 |
| 2006/0166167 A1 | * | 7/2006 | Syfrig | 433/152 |
| 2007/0218423 A1 | * | 9/2007 | Sapian | 433/152 |

* cited by examiner

*Primary Examiner* — Todd Manahan
*Assistant Examiner* — Matthew Nelson
(74) *Attorney, Agent, or Firm* — William Selenke

(57) ABSTRACT

The invention is an extractor for roots of broken teeth. This extractor has a square head spiral. That square head spiral has a spiral anchor and a square head with optional depressions in the sides of that square head. In that square head opposite the spiral anchor is a threaded hole. Included is a generally cubical square head socket with a lower square opening. There is a centrally located passage through the top of that generally cubical square head socket. The invention also has a thumb screw device with a rotator knob part and a threaded section. In operation the square head spiral anchor is screwed into the patient's broken tooth and the cubical square head socket is placed over the square head. The rotator knob part is threaded into the square head threaded hole. The extractor for roots of broken teeth is ready to remove the root of the broken tooth. The square head socket may have an extension. The invention includes a process for removing roots of broken teeth using the above device.

5 Claims, 6 Drawing Sheets

EXTRACTOR FOR BROKEN TOOTH ROOT

Provisional application No. 60/850,990 filed Oct. 11, 2006.

FIELD OF INVENTION

The invention is in the field of dentistry. More specifically it is concerned with the extraction of roots of broken teeth. It is not unusual that when a dentist removes a tooth, that tooth breaks leaving the root of the tooth in place. Often current methods used to remove the remaining tooth root can cause excessive trauma to the jaws.

BACKGROUND OF INVENTION

A dental problem occurs when the crown of a tooth breaks leaving the root of that tooth still embedded in the bone. This can be caused by two common dental techniques. In the first dental procedure, the dentist extracts a tooth by the traditional method of numbing the area around the diseased tooth with Novocain®. The dentist grasps the tooth using a special dental pliers or wrench. Using this tool and providing side movement, with twisting and upward forces, the dentist removes the tooth. If the tooth is weak and the bone matrix is strong the tooth will sometimes break leaving the root behind. In a second instance, when the dentist is mending or replacing the crown of the tooth, the crown of a tooth may be inadvertently fractured loose leaving the root in the jaw.

In either case the root that remains in jaw matrix must be removed for health reasons. To provide optimal healing that root should be removed with minimal damage to the bone matrix. This tooth root removal is important because dentists often replace the roots of teeth with titanium prosthesis. After a period of months the titanium implants become firmly anchored in the former root socket. Such a titanium implant can receive a replacement crown to produce a working artificial tooth. In the case of crown replacement, the tooth socket will heal much better if there is minimal bone matrix damage. Each of these conditions are addressed by the present invention and the prior art.

Prior art U.S. Pat. No. 6,019,602 teaches an extraction device for extracting the root of the tooth. The device includes an extraction bit having helical windings without a linear core portion separate from the windings, and in that manner is distinguishable from a common screw. A lockable and releaseable hand piece for attaching to the extraction bit provides leverage to the dentist for dislodging the tooth root, and is reversible in its attachment position to the extraction bit. U.S. Pat. No. 2,210,349 teaches a cone shaped helixical screw that will be placed into the root. A bridge over existing teeth and threaded screws will urge the tooth root up and out. Patent application 2006/0126741 teaches a variant on U.S. Pat. No. 2,210,349. The present invention essentially provides an artificial tooth crown with pits on the crown to receive the extraction pliers. This means that the dentist has fine control over the extraction process as if he were removing an intact tooth.

SUMMARY OF INVENTION

An extractor for roots of broken teeth has a square head with spiral. That head with spiral has a spiral anchor and a square head with optional depressions in the sides of that square head. In square head opposite the spiral anchor is a thread hole. Included is a cubical head socket with a lower square opening. There is a centrally located passage through the top of that cubical head socket. The invention also has a thumb screw device with a rotator knob part and a thread section. In operation the spiral anchor is screwed into the patient's broken tooth and the cubical head socket is placed over the square head and rotator knob part is threaded into the square head thread hole. The extractor for roots of broken teeth is ready to remove the root of the broken tooth. The square head socket may have an extension. The invention includes a process for removing roots of broken teeth comprising the steps of screwing a square head spiral anchor into a workpiece broken tooth. In square head opposite the spiral anchor is a thread hole. The dentist places a cubical square head socket over the square head, which square head socket has a lower square opening. Centrally located at the top of cubical head socket is a passage. The thumb screw device with a rotator knob part and a thread part is positioned above the square spiral head; the thread section is passed through the passage in the cubical socket. The thread section is screwed with rotator knob part into the head of the square head with spiral. The workpiece tooth root is removed by thumb screw device as it is moved upwardly by an attached rotator knob part into the square head socket which rests upon the bottom tooth gap created by a crown broken from the tooth root.

DETAILED DESCRIPTION OF FIGURES

Figure 1:
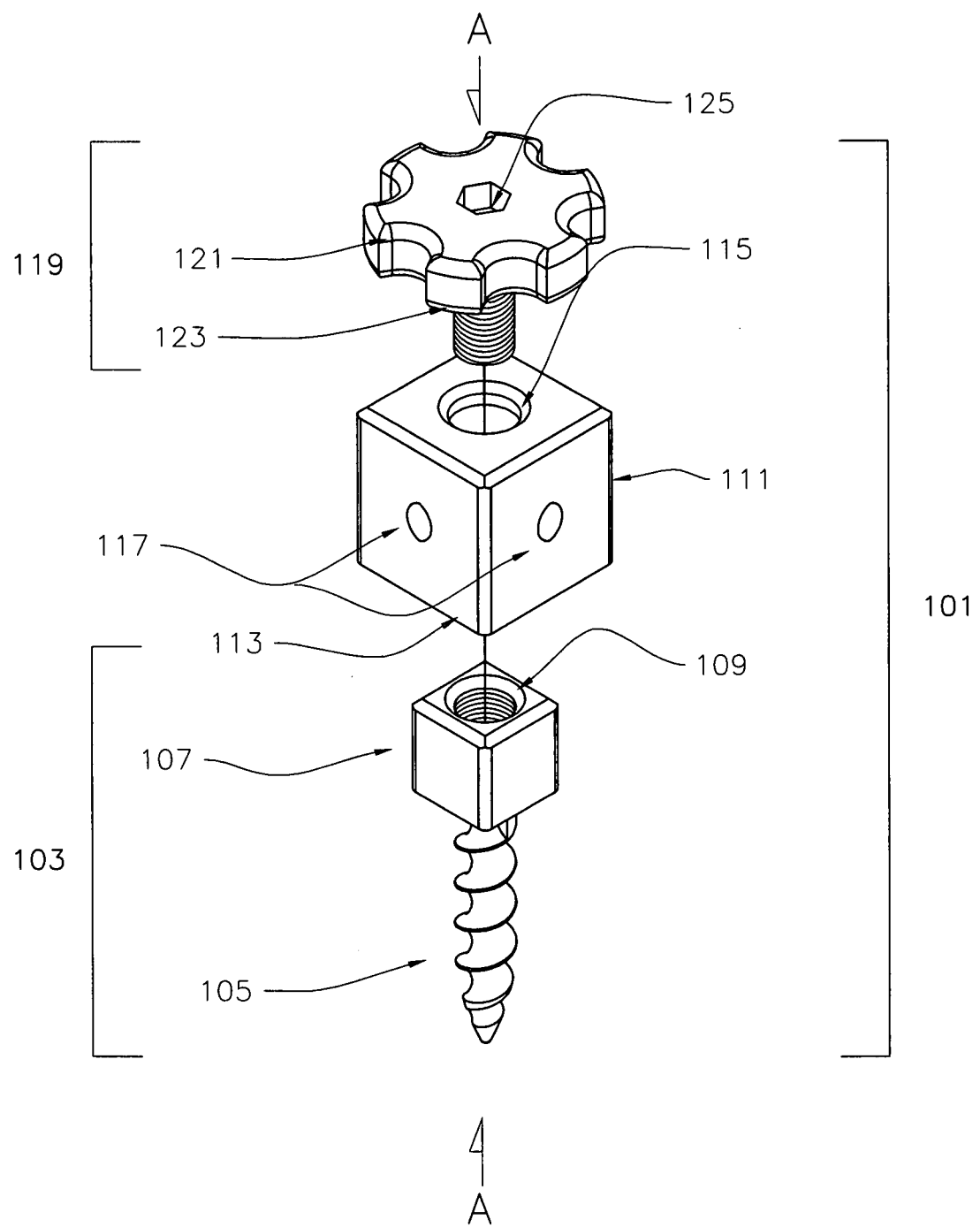
FIG. 1 shows an expanded view of the invention.

FIG. 1 shows an expanded view of the invention 101. The combination of square head 107 with spiral anchor 105 is square head/anchor combination 103. Square head 107 has a top, four sides, and a bottom. The bottom of square head 107 has a spiral anchor 105. A thread hole 109 is in the top opposite the attached spiral anchor 105 of square head 107. Cubical head socket 111 has a lower square opening 113. Placed into the sides of cubical head socket 111 are depressions 117. Centrally located through the top of cubical head socket 111 is passage 115. Thumb screw device 119 has a rotator knob part 121 and a thread section 123. Rotator knob part 121 has a hex screw receiving depression 125.

Figure 2:
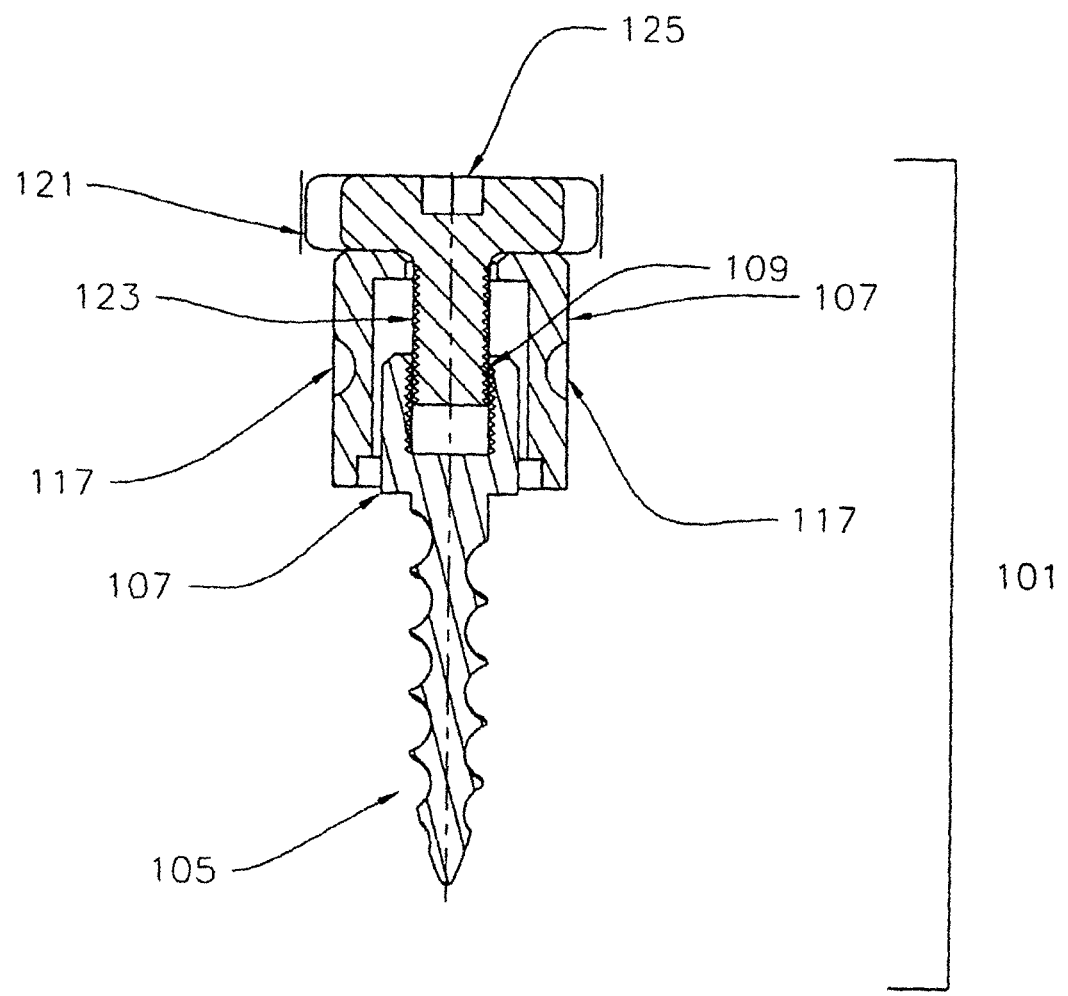
FIG. 2 shows assembled invention in section located by arrows AA in FIG. 1.

FIG. 2 shows assembled invention 101 in section located by arrows AA in FIG. 1. Likewise, FIG. 2 shows the invention assembled with thread section 123 threaded into thread hole 109 of square head 107. Depressions 117 are shown in cubical head socket 111. Rotator knob part 121 has a hex screw receiving depression 125. Spiral anchor 105 of square head 107 is shown.

Figure 3:
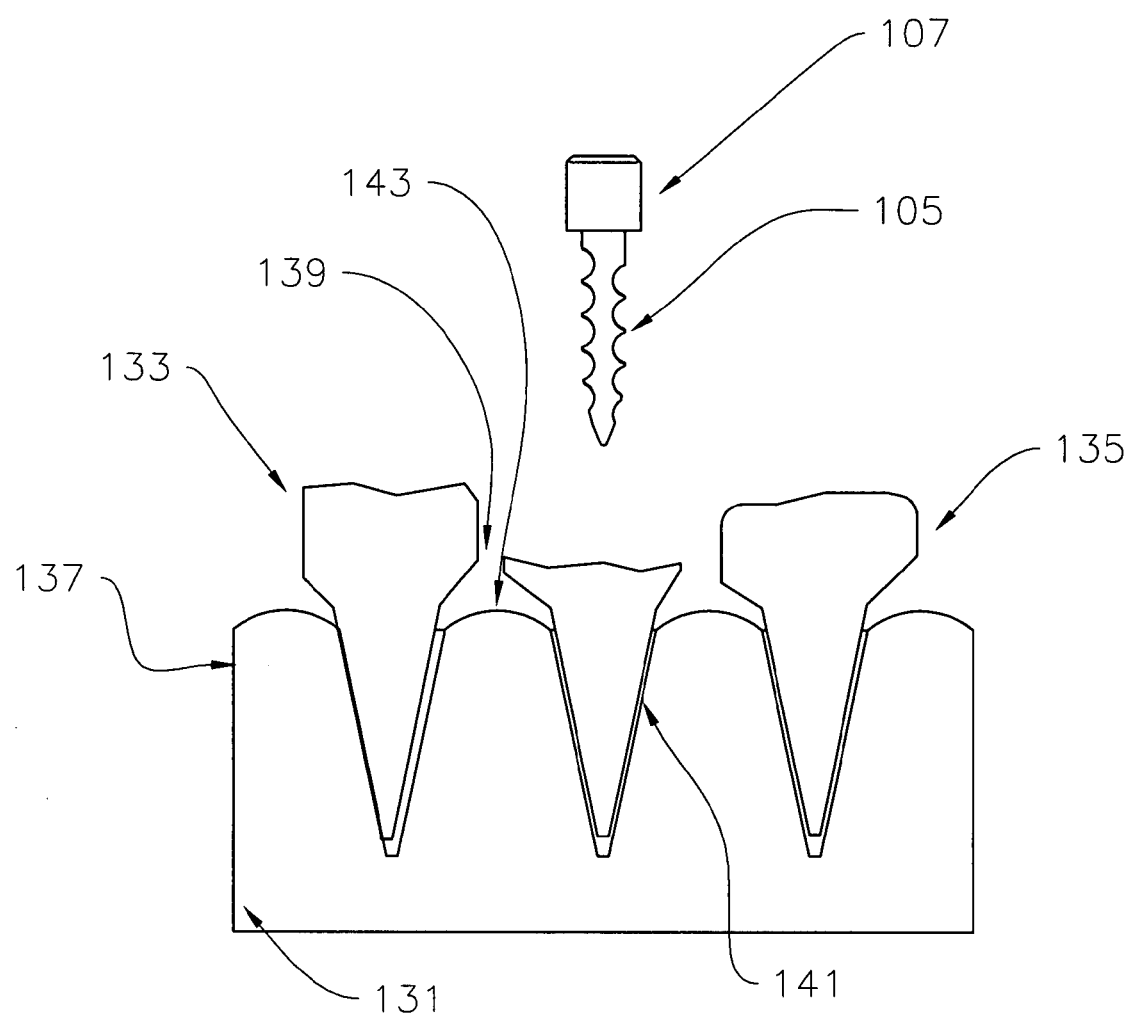
FIG. 3 shows square head with spiral anchor.

FIG. 3 shows square head 107 with spiral anchor 105 poised above workpiece jaw section 131. Workpiece jaw section 131 has a first tooth 133 and a second tooth 135 attached in jaw 137. Spiral anchor 105 of square head 107 is shown is shown between first tooth 133 and second tooth 135. Root fragment 141 is in the jaw and is the root of the tooth which was removed to make tooth gap 139.

Figure 4:
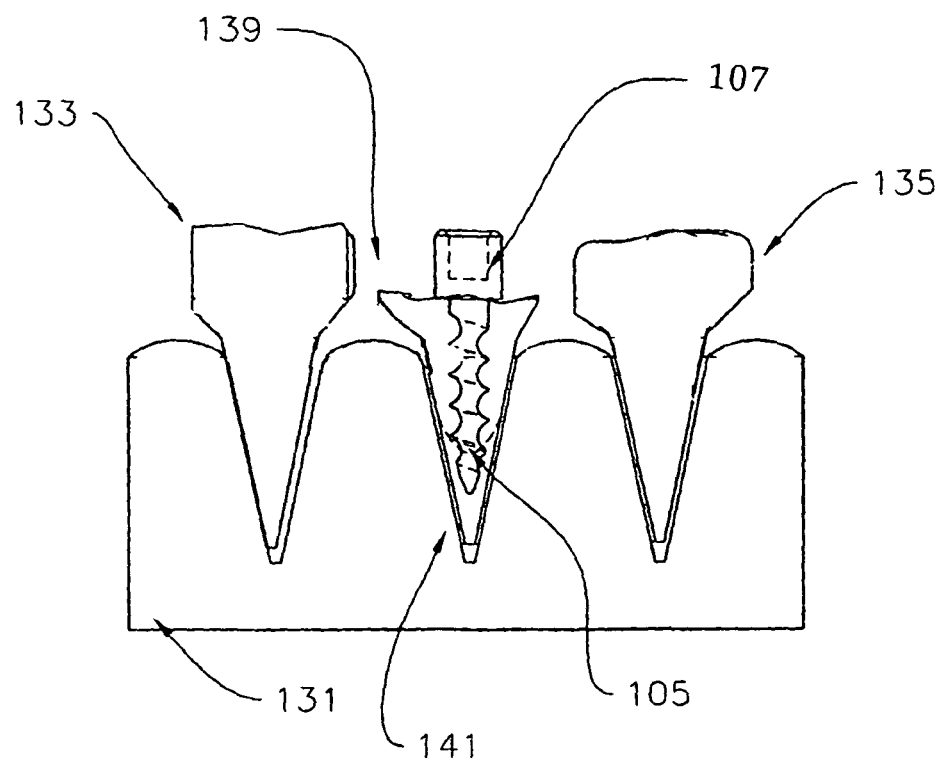
FIG. 4 shows first tooth, a second tooth with tooth gap.

FIG. 4 shows first tooth 133, a second tooth 135 with tooth gap 139. Square head 107 with spiral anchor 105 has been screwed into root fragment 141.

Figure 5:
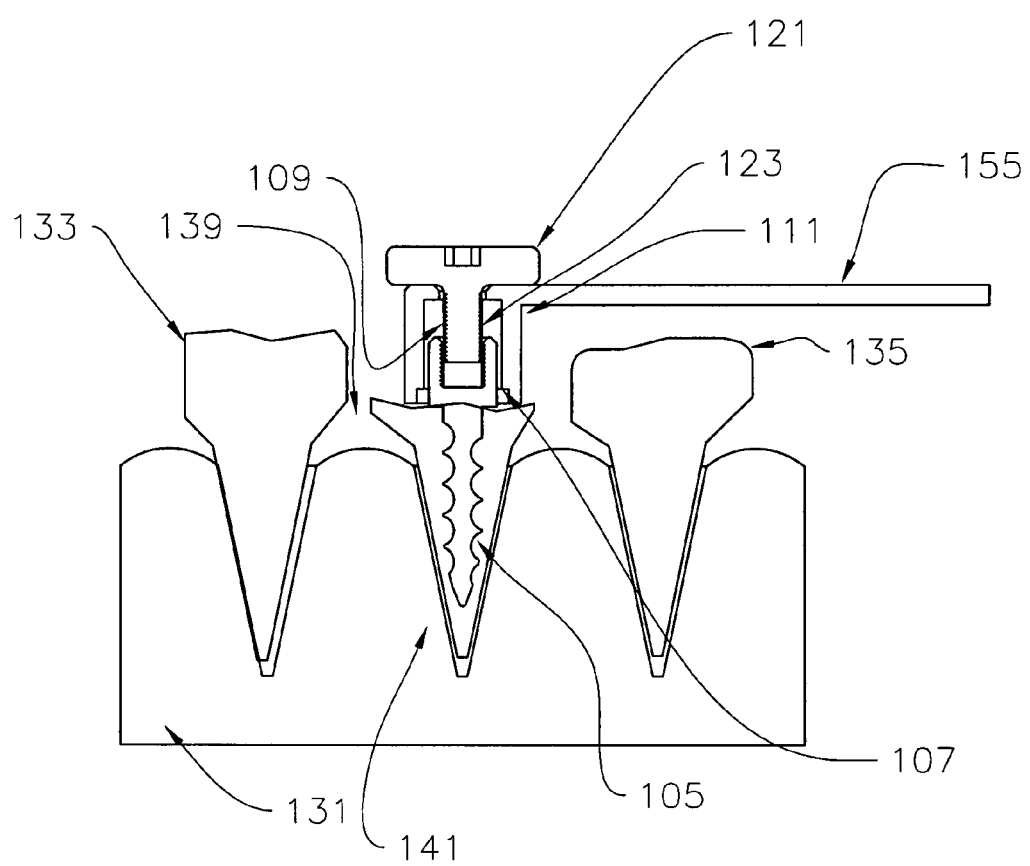
FIG. 5 shows invention assembled and in use.

FIG. 5 shows invention 101 assembled and in use. Spiral anchor 105 has been screwed into root fragment 141. Thumb screw device 119 has a rotator knob part 121 with attached thread section 123. Thread section 123 passes through passage 115 in square head 107 and is turned into threaded hole 109 in square head 107. Cubical head socket 111 rests upon the bottom 143 of tooth gap 139. Thus, cubical head socket 111 is supported by bottom 143 of tooth gap 139. As thumb screw device 119 rotator knob part 121 with thread section 123 is twisted into square head 107 the root 141 is urged up thus freeing the root. An optional extension 155 extents outward from a top side of square head 107. Optional extension 155 can aid the dentist in placing square head 107 on cubical head socket 111 and can aid in the extraction of the impacted root fragment 141.

Figure 6:
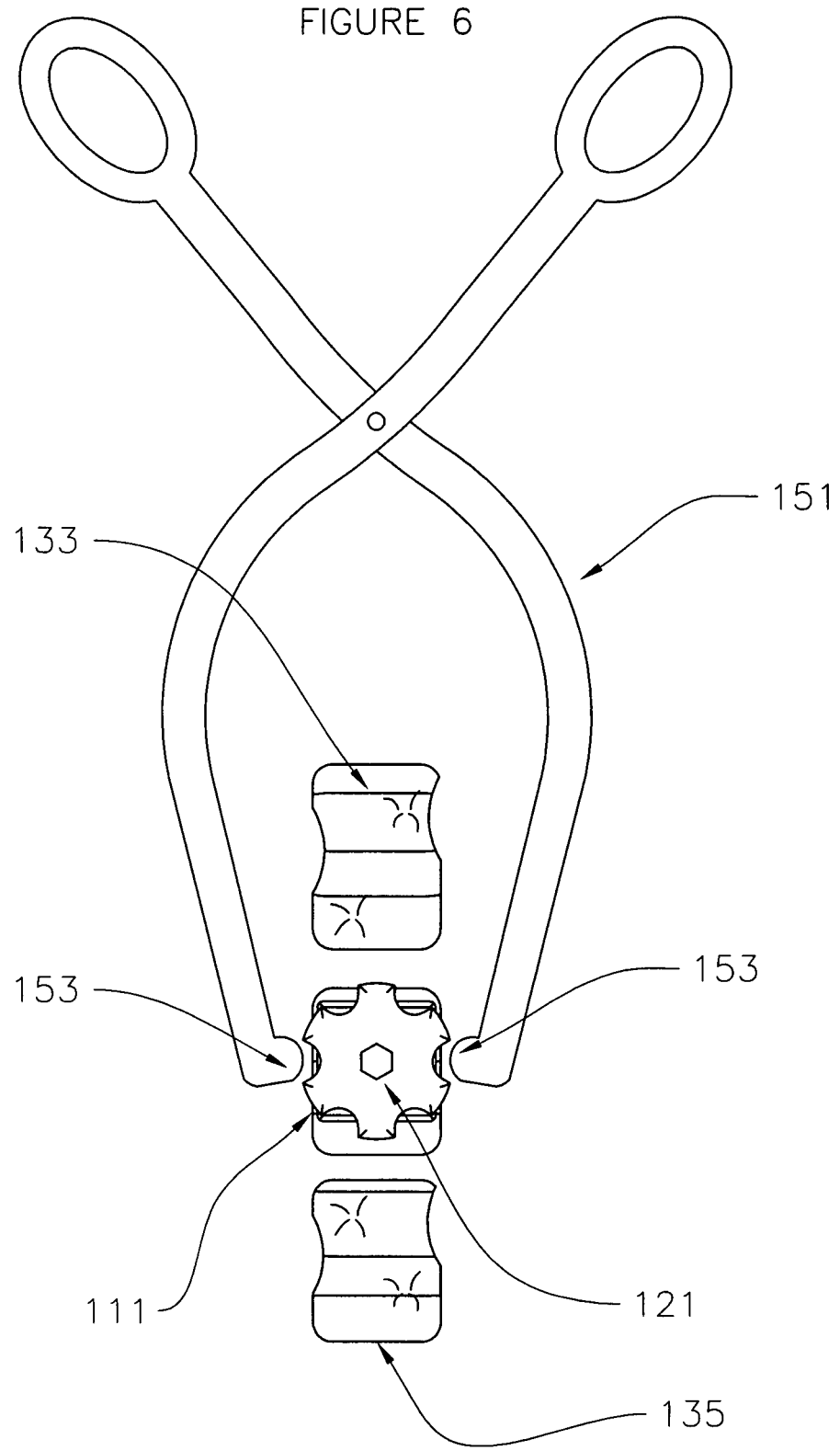
FIG. 6 shows a top view of an alternative use of the present invention in place as an artificial tooth.

FIG. 6 shows a top view of an alternative use of the present invention 101 in place as an artificial tooth. Rotator knob part 121 and cubical head socket 111 are shown between first tooth 133 and a second tooth 135. Workpiece extractor pliers 151 grasps the sides of square head 107 with depressions 117 as aids to anchor extractor pliers tips 153.

We claim:

1. An extractor for roots of broken teeth comprising:
   a square head spiral comprising a square head with a top, four sides, and a bottom; a spiral anchor adapted to be screwed into roots of broken teeth extends from the bottom; and a threaded hole is centrally located in the top opposite said spiral anchor;
   a cubical head socket comprising a top and a bottom; and a lower square opening in the bottom, the square opening having a cross-section complementary to that of the square head so as to snuggly receive the square head therein; a passage is centrally located in said cubical head socket extending through the top to the lower square opening; and
   a thumb screw device comprising a rotator knob part and a thread section, wherein the thread section is received in said passage to screw into the threaded hole of the square head, and thereby pull the square head up and into the cubical head socket.

2. An extractor for roots of broken teeth as in claim 1, wherein said cubical head socket further comprises depressions placed in said four sides for receiving extractor work piece pliers tips.

3. An extractor for roots of broken teeth as in claim 1, wherein said cubical head socket further comprises an extension.

4. A process for removing roots of broken teeth from a patient's jaw comprising the steps of:
   providing an extractor for roots of broken teeth comprising a square head spiral comprising a square head with a top, four sides, and a bottom; a spiral anchor extends from the bottom; and a threaded hole is centrally located in the top opposite said spiral anchor; a cubical head socket comprising a top and a bottom; and a lower square opening in the bottom, the square opening having a cross-section complementary to that of the square head so as to snuggly receive the square head therein; a passage is centrally located in said cubical head socket extending through the top to the lower square opening; and a thumb screw device comprising a rotator knob part and a thread section, wherein the thread section is received in said passage to screw into the threaded hole of the square head;
   screwing the spiral anchor into a workpiece broken tooth root;
   placing said cubical head socket over said square head to be supported by a bottom of a tooth gap created by a crown broken from said tooth root;
   screwing the thumb screw device thread section through the cubical head socket passage and into the square head threaded hole, thereby urging said square head and workpiece broken tooth root up into the cubical head socket and out of the patient's jaw.

5. A process for removing roots of broken teeth from a patient's jaw as in claim 4, wherein said cubical head socket further comprises depressions on its four sides for receiving extractor work piece pliers tips and further comprising the steps of grasping said depressions with work piece pliers tips and removing the extractor and workpiece broken tooth root with the work piece pliers.

* * * * *